United States Patent

Tihanyi et al.

Patent Number: 4,469,692
Date of Patent: Sep. 4, 1984

[54] SPIRO DERIVATIVES OF THE PYRAZOLO [1,5-D] [1,2,4] TRIAZINE RING SYSTEM AND A PROCESS FOR THE PREPARATION THEREOF

[75] Inventors: Endre Tihanyi; Ferenc Andrasi; Melinda Gál; Eleonóra Sineger, all of Budapest, Hungary

[73] Assignee: Alkaloida Vegyészeti Gyár, Budapest, Hungary

[21] Appl. No.: 442,451

[22] Filed: Nov. 17, 1982

[30] Foreign Application Priority Data

Nov. 18, 1981 [HU] Hungary .............................. 3445/81

[51] Int. Cl.³ .................. C07D 487/04; A61K 31/53; A61K 31/415
[52] U.S. Cl. .................................... 424/249; 544/184
[58] Field of Search .................... 544/184; 424/249

[56] References Cited

U.S. PATENT DOCUMENTS 3,840,537 10/1974 Garside et al. ....................... 544/184
4,168,964 9/1979 Walworth ........................... 544/184

Primary Examiner—John M. Ford
Attorney, Agent, or Firm—Keil & Weinkauf

[57] ABSTRACT

A spiro derivative of the pyrazolo [1,5-d] [1,2,4] triazine ring system of the formula I

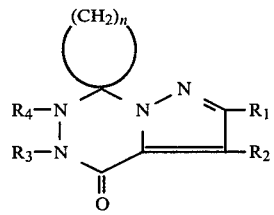

wherein
$R_1$ and $R_2$ represent, independently from each other, a hydrogen atom or a $C_{1-4}$ alkyl group,
$R_3$ stands for a hydrogen atom, an unbranched or branched $C_{1-4}$ alkyl, $C_{2-5}$ alkenyl or benzyl group,
$R_4$ represents a hydrogen atom, an unbranched or branched $C_{1-4}$ alkyl, $C_{4-6}$ cycloalkyl, an unsubstituted or mono-halo or polyhalo benzyl group, and
n is a whole number from 4 to 8, wherein R stands for an unbranched or branched $C_{1-4}$ alkyl, or $C_{4-6}$ cycloalkyl, $C_{2-5}$ alkenyl, an unsubstituted or a monohalogeno or polyhalogenobenzyl group, and X represents a halogen or a 4-methyl-phenylsulfonyloxy group. Compounds of the formula I exhibit valuable CNS activities.

7 Claims, No Drawings

SPIRO DERIVATIVES OF THE PYRAZOLO [1,5-D] [1,2,4] TRIAZINE RING SYSTEM AND A PROCESS FOR THE PREPARATION THEREOF

The invention relates to new spiro derivatives of the pyrazolo [1,5-d][1,2,4] triazine ring system of general formula I

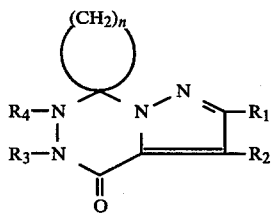

wherein
- $R_1$ and $R_2$ represent, independently from each other, a hydrogen atom or a $C_{1-4}$ alkyl group,
- $R_3$ stands for a hydrogen atom, an unbranched or branched $C_{1-4}$ alkyl, $C_{2-5}$ alkenyl or benzyl group,
- $R_4$ represents a hydrogen atom, an unbranched or branched $C_{1-4}$ alkyl, $C_{4-6}$ cycloalkyl, benzyl or a benzyl group substituted by one or more halogen atoms, and
- n means 4 to 8, and a process for the preparation thereof, furthermore to pharmaceutical compositions containing the same.

Accordingly, $R_1$ and $R_2$ can represent a hydrogen atom or a methyl group, $R_3$ can stand for a hydrogen atom, a methyl, ethyl, isopropyl, n-butyl, allyl or benzyl group, whereas $R_4$ can be a hydrogen atom, a methyl, isopropyl, cyclopentyl, cyclohexyl, benzyl or 2,6-dichlorobenzyl group.

The compounds covered by general formula I are new.

Some pyrazolo [1,5-d][1,2,4] triazine derivatives, showing some similarity to the compounds of general formula I, but devoid of the spiro-ring structural feature, are known compounds. They are prepared by the reaction of the corresponding pyrazolecarboxylic acid hydrazide and ortho-carboxylic ester or formaldehyde (J. Am. Chem. Soc. 7, 1148/1955/, and Heterocycles 14, 1291/1980/). The pharmacological activity of these compounds is unknown.

This invention is based on the finding that the compounds of general formula I exhibit valuable therapeutical, primarily CNS activities, and can be prepared from starting materials of general formula II.

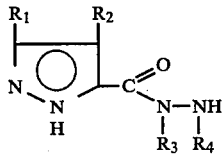

The invention provides a process for the preparation of new spiro derivatives of the pyrazolo [1,5-d][1,2,4] triazine ring system of general formula I, wherein $R_1$, $R_2$, $R_3$, $R_4$ and n have the same meaning as above, characterized by carrying out a reaction between a pyrazolecarboxylic acid hydrazide of general formula II, wherein $R_1$, $R_2$, $R_3$ and $R_4$ have the same meaning as above, and a cyclic ketone of general formula III

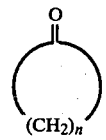

wherein n has the same meaning as above, and the resulting compounds of general formula I are optionally alkylated.

According to a preferred process of the invention the reaction between a compound of general formula II, wherein $R_1$, $R_2$, $R_3$ and $R_4$ have the same meaning as above, and a compound of general formula III, wherein n has the same meaning as above, is carried out in a solvent which is inert at these reaction conditions, preferably in an ether, such as dioxane, or in a hydrocarbon, such as benzene, toluene, xylene or in a halogeno hydrocarbon, such as chloroform, or in a mixture of these solvents, or without any solvent, at a temperature ranging from 0° C. to the boiling point of the reaction mixture, preferably around the boiling point of the solvent, and the resulting compounds of general formula I, wherein $R_1$, $R_2$, $R_3$, $R_4$ and n have the same meaning as above but either $R_3$ or $R_4$ represent a hydrogen atom, are alkylated with a compound of general formula IV, $$R-X \qquad (IV)$$

wherein R stands for an unbranched or branched $C_{1-4}$ alkyl, $C_{4-6}$ cycloalkyl, $C_{2-5}$ alkenyl, benzyl or a benzyl group substituted by one or more halogen atom, and X represents a halogen or a 4-methylphenyl-sulfonyloxy group, in a solvent which is inert at the reaction conditions applied, such as water, alkanols, hydrocarbons, halogeno-hydrocarbons, or in their mixture, in either a mono or biphasic system, or without any solvent, in the presence of an inorganic and/or organic base, at a temperature ranging from 0° C. to the boiling point of the reaction mixture, preferably at room temperature. Sodium methylate or sodium ethylate, tetrabutyl-ammonium hydroxide, triethyl-benzyl-ammonium hydroxide, this last mentioned base optionally in catalytic amounts, can be used as organic bases, while sodium or potassium hydroxide can be applied as inorganic bases.

The compounds of general formula II are known substances or can be prepared by procedures published in the literature (Gazz. Chim. Ital. 91, 1461–74/1961/).

The compounds of general formula III are known substances or can be prepared by known methods (Houben-Weyl: Methoden der Organischen Chemie, Ed. 4, Vol. 17/2a).

The compounds of general formula IV are known substances or can be prepared by known methods (Houben-Weyl: Methoden der Organischen Chemie, Ed. 4, Vol. 5/4, and Vol. 9).

The compounds of the invention, represented by general formula I and prepared by the procedure disclosed therein, exhibit valuable CNS activity.

The pharmacological potency of the compounds of general formula I is demonstrated on the example of spiro[cyclohexane-1,7'-/6,7-dihydro-2,5,6-trimethyl-pyrazolo[1,5-d][1,2,4]triazin-4(5H)-one/] selected for this purpose (Example 5). The hypnotic activity is measured by the method of Janssen et al. (J. Med. Chem. 8, 220/1965/). The results obtained on different animal species are summarized in the following tables. Ketalar/2-(2-chlorophenyl)-2-methyl-amino-cyclohexanone/ and Hexobarbital (5-methyl-5-hexenyl-barbituric acid) were applied as reference compounds.

TABLE 1

Hypnotic effect in mice. Comparative study of minimal hypnotic doses ($H_{min}$)

| COMPOUND | $H_{min}$ i.v. mg/kg | Mean duration of sleep* min. | $LD_{50}$ i.v. mg/kg | Therapeutic index $TI = \dfrac{LD_{50}}{H_{min}}$ |
|---|---|---|---|---|
| Spiro [cyclohexane-1,7'-/6,7-dihydro-2,5,6-trimethyl-pyrazolo[1,5-d]-[1,2,4]triazin-4(5H)-one/] | 25 | 6.75 | 192.5 | 7.7 |
| Ketalar (2-/2-chlorophenyl/-2-methyl-amino-cyclohexanone) | 25 | 5.0 | 62 | 2.5 |
| Hexobarbital (5-methyl-5-hexenyl-barbituric acid) | 45** | 7.2 | 117.5 | 2.6 |

$H_{min}$ = minimal hypnotic dose inducing sleep in all animals for a period exceeding 3 minutes
*in the case of dose $H_{min}$
**at a dose of 40 mg/kg the mean duration of sleep is only 2.6 minutes

TABLE 2

Hypnotic effect in mice. Comparative study of $HD_{50}$ values

| COMPOUND | $HD_{50}$ i.v. mg/kg | Mean duration of sleep* min. | $LD_{50}$ i.v. mg/kg | Therapeutic index $TI = \dfrac{LD_{50}}{HD_{50}}$ |
|---|---|---|---|---|
| Spiro [cyclohexane-1,7'-/6,7-dihydro-2,5,6-trimethyl-pyrazolo[1,5-d]-[1,2,4]triazin-4(5H)-one/] | 17.5 | 2.8 | 192.5 | 11 |
| Ketalar (2-/2-chlorophenyl/-2-methyl-amino-cyclohexanone) | 14.5 | 1.7 | 62 | 4.27 |
| Hexobarbital (5-methyl-5-hexenyl-barbituric acid) | 25 | 4.1 | 117.5 | 4.7 |

$HD_{50}$ = dose inducing sleep in 50 percent of the animals
*in the case of dose $HD_{50}$

TABLE 3

Hypnotic effect in rats

| COMPOUND | $HD_{50}$ i.v. mg/kg | Mean duration of sleep* min. | $LD_{50}$ i.v. mg/kg | Therapeutic index $TI = \dfrac{LD_{50}}{HD_{50}}$ |
|---|---|---|---|---|
| Spiro [cyclohexane-1,7'-/6,7-dihydro-2,5,6-trimethyl-pyrazolo[1,5-d]-[1,2,4]triazin-4(5H)-one/] | 16 | 1.5 | 275 | 17 |
| Ketalar (2-/2-chlorophenyl/-2-methyl-amino-cyclohexanone) | 8 | 1.9 | 39.4 | 4.9 |
| Hexobarbital (5-methyl-5-hexenyl-barbituric acid) | 17.5 | 4.45 | 125 | 7.14 |

*in the case of dose $HD_{50}$

TABLE 4

Hypnotic effect in rabbits

| COMPOUND | $H_{min}$ i.v. mg/kg | Mean duration of sleep* min. | $LD_{50}$ i.v. mg/kg |
|---|---|---|---|
| Spiro[cyclohexane-1,7'-/6,7-dihydro-2,5,6-trimethyl-pyrazolo[1,5-d]-[1,2,4]triazin-4(5H)-one/] | 25 | 5 | approx. 325 |
| Ketalar (2-/2-chlorophenyl/-2-methyl-amino-cyclohexanone) | 25 | 4 | <50 |

*in the case of dose $H_{min}$

The data of Tables 1 and 2 demonstrate that the hypnotic effect of the compound of the invention is superior to that of Hexobarbital and is in the same range as that of Ketalar, its toxicity, however, is substantially lower than that of any of the above reference substances.

Consequently, the therapeutic index of the compound of the invention, being a major indicator of the therapeutic value of a drug, is 2 to 3 times higher than that of the reference substances. Measured in rats the therapeutic index is more advantageous in both instances (Table 3).

Though in a dose of 25 mg/kg Ketalar induces a longer sleep in rabbits, already at a dose of 50 mg/kg 80 percent of the animals become killed, while the $LD_{50}$ of the compound of the invention can be expected to amount to 300 and 325 mg/kg (Table 4).

It is a further advantage of the compound of the invention over other known hypnotics that the postnarcotic period following awakening is rather short (max. 10 to 15 minutes), and devoid of any adverse effects.

The compounds of the invention can be applied both in human therapy and in veterinary practice as surgical narcotics. The new compounds can be utilized in the form of intravenous injections.

The dosage range applied can be 2.5 to 8 mg/kg body weight.

The finished pharmaceutical preparation can contain in addition to the active component a liquid, non-toxic vehicle generally applied in pharmaceutical formulations and it can be prepared by known methods.

The following examples are illustrative of the invention without limiting the disclosure.

EXAMPLE 1

Spiro[cyclohexane-1,7'-/6,7-dihydro-2,6-dimethyl-pyrazolo[1,5-d,][1,2,4]triazin-4(5H)-one/]

The mixture of 9.3 g of 3(5),N'-dimethyl-1H-pyrazole-5(3)-carboxylic acid hydrazide and 19 ml of cyclohexanone is heated under reflux for two hours. The reaction mixture is cooled and 120 ml of petroleum ether (b.p. 40° to 70° C.) are added at stirring. The crystals formed are filtered, washed with petroleum ether, and are recrystallized from isopropanol following drying. Yield 11.85 g (84.4 percent). M.p. 167° to 169° C.

EXAMPLE 2

Spiro[cyclopentane-1,7'-/6,7-dihydro-2,6-dimethyl-pyrazolo[1,5-d][1,2,4]triazin-4(5H)-one/]

The mixture of 5 g of 3(5),N'-dimethyl-1H-pyrazole-5(3)-carboxylic acid hydrazide and 12.5 ml of cyclopentanone is refluxed for 3 hours. The reaction mixture is cooled and 75 ml of petroleum ether (b.p. 40° to 70° C.)

are added. The crystals formed are filtered, washed with petroleum ether and recrystallized from a mixture of benzene-petroleum ether. Yield 3.94 g (55.2 percent). M.p. 128° to 130° C.

EXAMPLE 3

Spiro[cycloheptane-1,7'-/6,7-dihydro-2,6-dimethyl-pyrazolo[1,5-d][1,2,4]triazin-4(5H)one/]

The mixture of 5 g of 3(5),N'-dimethyl-1H-pyrazole-5(3)-carboxylic acid hydrazide and 10 ml of cycloheptanone is heated under reflux for 6 hours. The crystals precipitated from the cooled reaction mixture are filtered, washed with petroleum ether, and recrystallized from a mixture of benzene-petroleum ether. Yield 2.93 g (36.4 percent). M.p. 80° to 82° C.

EXAMPLE 4

Spiro[cyclohexane-1,7'-/6,7-dihydro-2,5-dimethyl-pyrazolo-[1,5-d][1,2,4]-triazin-4(5H)-one/]

1,5 g of 3(5),N'-dimethyl-1H-pyrazole-5(3)-carboxylic acid hydrazide is dissolved in 7.5 ml of cyclohexanone, and the resulting solution agitated for 3 hours at room temperature. The solution is either inoculated with a crystal or the wall of the flask is scratched with a glass rod to induce crystallizing, then stirring is continued for further two hours, the suspension is filtered and the crystals washed with petroleum ether. Yield 1.39 g (61.7 percent). M.p. 70° to 72° C.

EXAMPLE 5

Spiro[cyclohexane-1,7'-/6,7-dihydro-2,5,6-trimethyl-pyrazolo[1,5-d][1,2,4]triazin-4(5H)-one/]

0.7 g of metal sodium, dissolved in 30 ml of methanol, and 5.6 g p-toluenesulfonic acid methyl ester are added to 7 g of spiro[cyclohexane-1,7'-/6,7-dihydro-2,6-dimethyl-pyrazolo[1,5-d][1,2,4]triazin-4(5H)-one/] (Example 1), dissolved in 90 ml of methanol. The solution is stirred for three hours at room temperature and then a further portion of 0.7 g of metal sodium, dissolved in 30 ml of methanol, and 5,6 g p-toluenesulfonic acid methyl ester are added. Stirring is continued for further three hours at room temperature. The mixture is filtered, then the methanol is evaporated. The residue is taken up in a mixture of 100 ml of chloroform and 20 ml of water, the phases are separated and the aqueous extraction is repeated three more times. The chloroform layer is dried and evaporated to dryness. Yield 6.54 g (87.9 percent). M.p. 80° to 82° C.

EXAMPLE 6

Spiro[cyclohexane-1,7'-/6,7-dihydro-2,6-dimethyl-5-ethyl-pyrazolo[1,5-d][1,2,4]triazin-4(5H)-one/]

Method a 2.34 g of spiro[cyclohexane-1,7'-/6,7-dihydro-2,6-dimethyl-pyrazolo[1,5-d][1,2,4]triazin-4(5H)-one/] (Example 1), 3.4 g of tetrabutyl-ammonium-hydrogen sulfate and 2 ml of ethyl iodide are dissolved in a mixture of 20 ml of 20 percent sodium hydroxide and 20 ml of chloroform, and the system is stirred for 12 hours at room temperature. The two layers are separated, the chloroform layer is washed 6 times with 3 ml of water, then is evaporated following drying. The resulting product is worked up with ether (20 ml) and is filtered. The ether is evaporated yielding 2.0 g (76.3 percent) of the product, m.p. 88° to 90° C.

Method b 2.34 g of spiro[cyclohexane-1,7'-/6,7-dihydro-2,6-dimethyl-pyrazolo[1,5-d][1,2,4]triazin-4(5H)-one/] are dissolved in 10.9 ml of a potassium hydroxide solution in methanol (potassium hydroxide content 10.25 g/100 ml). 1 ml of ethyl iodide is added to this solution and is stirred for 1 hour at room temperature, then a further portion of 1 ml of ethyl iodide is added, and the stirring is continued for further 2 hours. Finally the reaction mixture is left to stand overnight. After filtering the filtrate is evaporated, the residue is taken up in a mixture of 40 ml of chloroform and 20 ml of water and is separated. The chloroform layer is washed four more times with 20 ml of water. The chloroform layer is dried and evaporated. Yield 2.30 g (90.8 percent). M.p. 88° to 90° C.

EXAMPLE 7

Spiro[cyclohexane-1,7'-/6,7-dihydro-2,6-dimethyl-5-benzyl-pyrazolo[1,5-d][1,2,4]triazin-4(5H)-one/]

Method a 1.17 g of spiro[cyclohexane-1,7'-/6,7-dihydro-2,6-dimethyl-pyrazolo[1,5-d][1,2,4]triazin-4(5H)-one/] (Example 1) is dissolved in 50 ml of ethanol and a solution of 0.23 g of metal sodium in 10 ml of ethanol is added, then 0.55 ml of benzylchloride is given to the solution which is agitated for 1 hour at room temperature. Then a further portion of 0.55 ml of benzylchloride is added to the reaction mixture and the stirring is continued for further three hours, then the system is left to stand overnight. The mixture is filtered and the filtrate evaporated. The residue is taken up in a mixture of 20 ml of chloroform and 10 ml of water, the layers are separated, and the chloroform layer is extracted three more times with 10 ml of water. The chloroform layer is dried, evaporated and the residue is recrystallized from methanol. Yield 1.05 g (64.7 percent). M.p. 125° to 127° C.

Method b

The mixture consisting of 1.17 g of spiro[cyclohexane-1,7'-/6,7-dihydro-2,6-dimethyl-pyrazolo[1,5-d][1,2,4]-triazin-4(5H)-one/], 1.1 ml of benzylchloride, 0.1 g of triethyl-benzyl-ammonium chloride, 2 g of sodium hydroxide, 10 ml of chloroform and 10 ml of water is stirred for 5 hours at room temperature. The layers are separated, the chloroform layer is washed five times with 5 ml of water, dried and evaporated. The residue is recrystallized from methanol. Yield 1.2 g (73.9 percent). M.p. 124° to 126° C.

The procedures disclosed in Examples 1 to 7 were applied to prepare the following compounds summarized in Table 5.

TABLE 5

| Example No. | COMPOUND | M.p. C.° |
|---|---|---|
| 8 | Spiro[cyclopentane-1,7'-/6,7-dihydro-6-cyclopentyl-2-methyl-pyrazolo[1,5-d][1,2,4]triazin-4(5H)-one/] | 162–164 |
| 9 | Spiro[cyclopentane-1,7'-/6,7-dihydro-2,5,6-trimethyl-pyrazolo[1,5-d][1,2,4]triazin-4(5H)-one/] | 82–83 |
| 10 | Spiro[cyclohexane-1,7'-/6,7-dihydro-2-methyl-6-isopropyl-pyrazolo[1,5-d][1,2,4]triazin-4(5H)-one/] | 166–167 |
| 11 | Spiro[cyclohexane-1,7'-/6,7-dihydro-6-cyclopentyl-2-methyl-pyrazolo[1,5-d][1,2,4]triazin-4(5H)-one/] | 203–205 |

TABLE 5-continued

| Example No. | COMPOUND | M.p. °C. |
|---|---|---|
| 12 | Spiro[cyclohexane-1,7'-/6,7-dihydro-6-cyclohexyl-2-methyl-pyrazolo[1,5-d][1,2,4]triazin-4(5H)-one/] | 215–217 |
| 13 | Spiro[cyclohexane-1,7'-/6,7-dihydro-6-(2,6-dichlorobenzyl)-2-methyl-pyrazolo[1,5-d][1,2,4]triazin-4(5H)-one/] | 240–242 |
| 14 | Spiro[cyclohexane-1,7'-/6,7-dihydro-2,5-dimethyl-6-isopropyl-pyrazolo[1,5-d][1,2,4]triazin-4(5H)-one/] | 55–57 |
| 15 | Spiro[cyclohexane-1,7'-/6,7-dihydro-6-cyclohexyl-2,5-dimethyl-pyrazolo[1,5-d][1,2,4]triazin-4(5H)-one/] | 157–159 |
| 16 | Spiro[cyclohexane-1,7'-/6,7-dihydro-6-(2,6-dichlorobenzyl)-5-methyl-pyrazolo[1,5-d][1,2,4]triazin-4(5H)-one/] | 231–232 |
| 17 | Spiro[cyclohexane-1,7'-/6,7-dihydro-2,6-dimethyl-5-isopropyl-pyrazolo[1,5-d][1,2,4]-triazin-4(5H)-one/] | 80–82 |
| 18 | Spiro[cyclohexane-1,7'-/6,7-dihydro-5-n-butyl-2,6-dimethyl-pyrazolo[1,5-d][1,2,4]triazin-4(5H)-one/] | 89–91 |
| 19 | Spiro[cyclohexane-1,7'-/6,7-dihydro-3,6-dimethyl-pyrazolo[1,5-d][1,2,4]triazin-4(5H)-one/] | 166–168 |
| 20 | Spiro[cyclohexane-1,7'-/6,7-dihydro-3,5,6-trimethyl-pyrazolo[1,5-d][1,2,4]triazin-4(5H)-one/] | 133–135 |
| 21 | Spiro[cycloheptane-1,7'-/6,7-dihydro-2,5,6-trimethyl-pyrazolo[1,5-d][1,2,4]triazin-4(5H)-one/] | 104–106 |
| 22 | Spiro[cyclohexane-1,7'-/6,7-dihydro-6-benzyl-2-methyl-pyrazolo[1,5-d][1,2,4]triazin-4(5H)-one/] | 103–105 |
| 23 | Spiro[cyclohexane-1,7'-/6,7-dihydro-5-allyl-2,6-dimethyl-pyrazolo[1,5-d][1,2,4]triazin-4(5H)-one/] | 59–61 |

EXAMPLE 24

Preparation of a pharmaceutical composition

The contents of one ampoule are the following:

| | |
|---|---|
| Spiro[cyclohexane-1,7'-/6,7-dihydro-2,5,6-trimethyl-pyrazolo[1,5-d][1,2,4]triazin-4(5H)-one/] | 250 mg |
| Ethoxylated castor oil* | 1 ml |
| Physiological solution of sodium chloride ad (USP XX) | 5 ml |

*Can be purchased from BASF AG (Ludwigshafen, FRG), registered name Chremophor EL.

What we claim is:
1. A spiro derivative of the pyrazolo[1,5-d][1,2,4]triazine ring system of the formula I

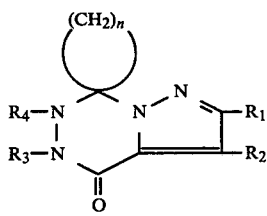

wherein
$R_1$ and $R_2$ represent, independently from each other, a hydrogen atom or a $C_{1-4}$ alkyl group,
$R_3$ stands for a hydrogen atom, an unbranched or branched $C_{1-4}$ alkyl, $C_{2-5}$ alkenyl or benzyl group,
$R_4$ represents a hydrogen atom, an unbranched or branched $C_{1-4}$ alkyl, $C_{4-6}$ cycloalkyl, benzyl or a benzyl group substituted by one or more halogen atom, and
n means 4 to 8.

2. Spiro[cyclohexane-1,7'-/6,7-dihydro-2,5,6-trimethyl-pyrazolo[1,5-d][1,2,4]triazin-4(5H)-one/].

3. A process for the preparation of a spiro derivative of the pyrazolo[1,5-d][1,2,4]triazine ring system of the formula I

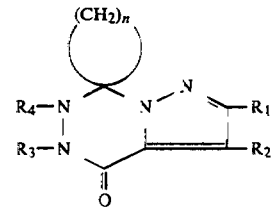

wherein
$R_1$ and $R_2$ represent, independently from each other, a hydrogen atom or a $C_{1-4}$ alkyl group,
$R_3$ stands for a hydrogen atom, an unbranched or branched $C_{1-4}$ alkyl, $C_{2-5}$ alkenyl or benzyl group,
$R_4$ represents a hydrogen atom, an unbranched or branched $C_{1-4}$ alkyl, $C_{4-6}$ cycloalkyl, benzyl or a benzyl group substituted by one or more halogen atoms, and
n means 4 to 8, characterized by carrying out a reaction between a pyrazolecarboxylic acid hydrazide of general formula II

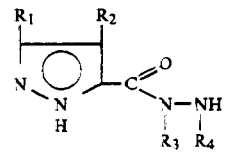

wherein
$R_1$, $R_2$, $R_3$, and $R_4$ have the same meaning as above, and a cyclic ketone of the formula III

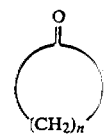

wherein
n has the same meaning as above, in a solvent or without any solvent, and the resulting compounds of general formula I, wherein $R_1$, $R_2$, $R_3$, $R_4$ and n have the same meaning as above but either $R_3$ or $R_4$ represent a hydrogen atom, are optionally alkylated with a compound of the formula IV

R—X      (V)

wherein R stands for an unbranched or branched $C_{1-4}$ alkyl, or $C_{4-6}$ cycloalkyl, $C_{2-5}$ alkenyl, benzyl or a benzyl group substituted by one or more halogen atom, and X represents a halogen or a 4-methyl-phenyl-sulfonyloxy group, in the presence of an inorganic and/or organic base.

4. A process as claimed in claim 5, characterized by using an excess amount of the compound of the formula III as solvent.

5. A process as claimed in claim 3, characterized by alkylating the compounds of the formula I, wherein $R_1$, $R_2$, $R_3$, $R_4$ and n have the same meaning as above but $R_3$ or $R_4$ or both represent a hydrogen atom, in the presence of potassium or sodium hydroxide and a quaternary ammonium base, preferably tetrabutyl-ammonium-hydroxide or triethyl-benzyl-ammonium-hydroxide, in a two-phase system.

6. A pharmaceutical composition for use as a CNS depressant and containing as active ingredient an effective amount of at least one compound of the formula I, of claim 1, and a conventional inert, non-toxic, solid or liquid carrier and/or additive.

7. A method of depressing CNS activity in a patient which comprises: administering to said patient the pharmaceutical composition of claim 6 in a dosage amount of active ingredient of from 2.5 to 8 mg/kg in body weight.

* * * * *